United States Patent
Smallridge et al.

(12) 
(10) Patent No.: US 7,176,332 B2
(45) Date of Patent: Feb. 13, 2007

(54) METHODS FOR THE SYNTHESIS OF AMINES SUCH AS EPHEDRINE AND INTERMEDIATES

(75) Inventors: Andrew John Smallridge, Victoria (AU); Maurice Arthur Trewhella, Victoria (AU); Kylie Anne Wilkinson, Victoria (AU)

(73) Assignees: Victoria University of Technology, Footscray (AU); Polychip Pharmaceuticals Pty. Ltd., Toorak (AU)

( * ) Notice: Subject to any disclaimer, the term of this patent is extended or adjusted under 35 U.S.C. 154(b) by 0 days.

(21) Appl. No.: 10/488,034

(22) PCT Filed: Aug. 26, 2002

(86) PCT No.: PCT/AU02/01148

§ 371 (c)(1),
(2), (4) Date: Jul. 27, 2004

(87) PCT Pub. No.: WO03/018531

PCT Pub. Date: Mar. 6, 2003

(65) Prior Publication Data

US 2004/0249212 A1    Dec. 9, 2004

(30) Foreign Application Priority Data

Aug. 28, 2001   (AU) .................................. PR7326

(51) Int. Cl.
*C07C 209/26* (2006.01)

(52) U.S. Cl. ....................... 564/397; 564/398; 564/472

(58) Field of Classification Search ...................... None
See application file for complete search history.

(56) References Cited

U.S. PATENT DOCUMENTS 1,956,950 A    5/1934    Hildebrandt et al.

FOREIGN PATENT DOCUMENTS

| EP | 0 099 416 | 7/1982 |
|---|---|---|
| EP | 1142864 | 10/2001 |
| WO | WO 97/12928 | 4/1997 |
| WO | WO 97/38955 | 10/1997 |
| WO | WO 00/39071 | 7/2000 |
| WO | WO 01/44486 | 6/2001 |

OTHER PUBLICATIONS

Database CAPLUS on STN, Acc. No. 1999:422871, Kordikowski et al., Journal of Pharmaceutical Sciences (1999), 88(8), p. 786-791 (abstract).*
Database CAPLUS on STN, Acc. No. 2001:223123, Kim et al., Korean Journal of Chemical Engineering (2000), 17(6), p. 672-677 (abstract).*
European Search Report from European Patent Application No. 02764370.9, dated Dec. 2, 2004.

* cited by examiner

*Primary Examiner*—Brian Davis
(74) *Attorney, Agent, or Firm*—Klarquist Sparkman, LLP

(57) ABSTRACT

A method for the preparation of a compound of formula (VI): in which $R_2$ is an optionally substituted C1–C6 alkyl; $R_4$ is H, OH, an optionally substituted C1–C6 alkyl or an optionally substituted C1–C6 alkoxy; $R_5$ is an optionally substituted aryl, an optionally substituted aralkyl, or an optionally substituted alkyl; and $R_6$ is H or an optionally substituted C1–C6 alkyl; the method including the step of subjecting a ketone of formula (V) in which $R_2$, $R_4$ and $R_5$ are as defined above, to reductive amination with an amine of formula $R_3NH_2$ in which $R_3$ is an optionally substituted alkyl, and a reductant to form the compound of formula (VI), wherein the reaction is conducted in the presence of a supercritical fluid or a liquefied gas.

19 Claims, No Drawings

METHODS FOR THE SYNTHESIS OF AMINES SUCH AS EPHEDRINE AND INTERMEDIATES

CROSS REFERENCE TO RELATED APPLICATIONS

This is the U.S. National Stage of International Application No. PCT/AU02/01148, filed Aug. 26, 2002, which was published in English under PCT Article 21(2), which in turn claims the benefit of Australian Provisional Application No. PR7326, filed Aug. 28, 2001.

The present invention relates to new environments in which to conduct certain classes of chemical reactions. The present invention particularly relates to new methods and environments for the synthesis of useful pharmaceutical compounds such as ephedrine.

BACKGROUND OF THE INVENTION

A range of important classes of pharmaceutical compounds, food additives and other biologically active compounds are based on chiral alkyl amines. Such classes of compounds include the sympathomimetic amines, such as ephedrine ($\alpha$-[1-(methylamino)ethyl]benzene-methanol). Many of these compounds are commercially important and are synthesised for use in pharmaceutical compositions and in other applications.

Physicochemical methods for production of enantiomerically pure compounds usually involve multi-step synthesis incorporating one or more steps which are asymmetric, and laborious purification procedures. Such methods are not only tedious, but frequently provide relatively poor yields. Alternatively enantiomerically-pure starting materials can be used, together with enantioselective reaction steps; however, such pure starting materials are available only for a very limited number of desired compounds.

In recent years, intense efforts have been directed towards development of methods which are highly selective, provide a good rate of transformation, and enable easy, non-chromatographic separation and purification of the product. It has also been considered particularly desirable for the reactions to be carried out in non-aqueous solvents, since these are particularly convenient for large scale reactions and purifications.

Ephedrine ($\alpha$-[1-(methylamino)ethyl]benzene-methanol), originally isolated from plants of the genus *Ephedra*, occurs as the naturally-occurring isomers 1-ephedrine and d-pseudoephedrine, and other pharmacologically active isomers include d-ephedrine and 1-pseudoephedrine. These compounds are adrenergic sympathomimetic agents and have antihistamine activity; 1-ephedrine is widely used as a bronchodilator, while d-pseudoephedrine is widely used as a decongestant. Compounds of these groups are present in a very wide range of prescription and over-the-counter pharmaceutical formulations.

The production of 1-phenylacetylcarbinol, a precursor of 1-ephedrine, by catalysis using whole baker's yeast cells in aqueous medium was one of the first microbial biotransformation processes to be used commercially (Neuberg and Hirsch, 1921; see also Hildebrandt and Klavehn, 1934). This reaction involves the yeast-induced condensation of benzaldehyde with acetyl-coenzyme A. The reaction has been widely investigated, and has been shown to be mediated by the enzyme pyruvate decarboxylase (Groger, Schmander and Mothes, 1966). It has also been shown that the reaction has a relatively broad specificity for the substrate, enabling a variety of substituted aromatic aldehydes to be converted to the corresponding substituted optically-active phenylacetylcarbinols (Long, James and Ward, 1989).

Although this yeast-catalysed system has been widely exploited, this has normally utilised aqueous systems, which are inconvenient for large-scale extraction and purification, which require organic solvents. Additionally, fermentation systems present the disadvantage that purification of the desired product can be difficult, and yields tend to be low; while the yield and convenience of the reaction can be improved by utilising immobilised cells, or cells which have been selected or genetically, modified, this adds significantly to the cost of the process. The use of purified enzymes is normally prohibitively expensive, and again without the use of immobilised enzymes the yields tend to be low and purification difficult.

In our earlier International Application PCT/AU00/01543, we showed that yeast-mediated acyloin condensation of benzaldehyde can be achieved in supercritical or liquefied carbon dioxide or in liquefied petroleum gas. This reaction results in superior conversion of the aromatic aldehydes to the desired carbinol when compared with the corresponding reaction conducted in conventional organic solvents. In a preferred embodiment, yields of around 79% with the total absence of side-products were obtained using the method of the invention.

Based on experiments with other ketones and aldehydes, it was believed that reductive amination of the carbinol could not be conducted in any mediums other than conventional organic solvents. Accordingly, the difficulty still remained that the intermediate had to be converted into 1-ephedrine using conventional techniques in conventional organic solvents.

It has now surprisingly been found by the present applicant that reductive amination of the ketone precursor for ephedrine can be conducted in the presence of supercritical fluids or liquefied gases such as supercritical carbon dioxide or liquefied petroleum gas. These reagents are especially advantageous to use as the reaction medium in large scale reactions since the purification and processing of the products is simpler than comparable reactions conducted in standard organic or aqueous solvents.

Similarly, the applicant has found that particular ketone precursors for compounds structurally related to ephedrine can be subjected to reductive amination to form the target amines in supercritical fluids or liquefied gases.

Since carbon dioxide is non-toxic and can be readily recycled, this method avoids the problems associated with reactions involving organic solvents. Moreover, when combined with earlier reactions or processes conducted in the same solvent, the target compound can be made in a "one-pot" process, thereby further maximising possible yields and simplifying large scale operations for the synthesis of the compound.

SUMMARY OF THE INVENTION

According to one aspect of the present invention there is provided a method for the formation of an amine of formula (VI):

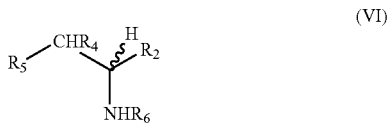

wherein $R_2$ is optionally substituted C1–C6 alkyl;
$R_4$ is H, OH, optionally substituted C1–C6 alkyl or optionally substituted C1–C6 alkoxy;
$R_5$ is optionally substituted aryl, optionally substituted aralkyl, or optionally substituted alkyl; and
$R_6$ is H or an optionally substituted C1–C6 alkyl;

the method including the step of reacting a ketone of formula (V)

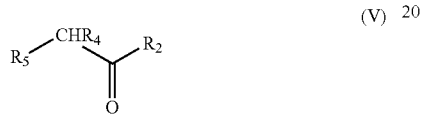

in which $R_2$, $R_4$ and $R_5$ are as defined above, with a primary amine of formula $R_3NH_2$ in which $R_3$ is an optionally substituted alkyl, and a reductant, in the presence of a supercritical fluid or a liquefied gas, to form the amine of formula (VI).

This method may be represented by the following reaction scheme:

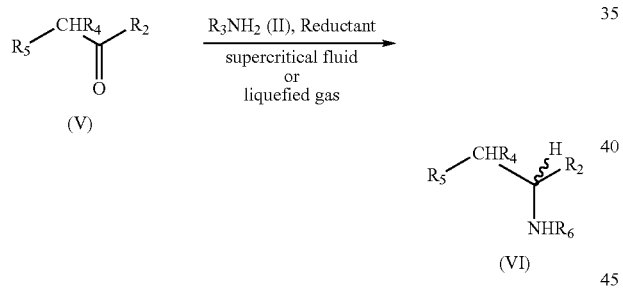

Preferably, the reductant is $H_2$ and the reduction is conducted in the presence of a suitable catalyst (so that $R_6$ is $R_3$). However, another option is to utilise a hydride reducing agent such as $NaBH_4$ or $LiAlH_4$. With the appropriate selection of the amine reagent II (ie $R_3$) and hydride reducing agent, the group $R_3$ which is initially present in the enamine intermediate formed is removed during the reduction step, so that $R_6$ will be H. With the selection of other $R_3$ groups and appropriate hydride reducing agent, this does not occur, so that $R_6$ will be $R_3$. The reducing reagent(s) can be added to the reaction mixture together with the secondary amine of formula (II), or in a subsequent step.

According to one embodiment of the invention, the amine (VI) is selected from the group consisting of ephedrine ($R_4$=OH, $R_5$=phenyl, $R_2$=methyl, $R_6$=$R_3$=methyl), isoetharine ($R_4$=OH, $R_5$=3,4-dihydroxyphenyl, $R_2$=ethyl, $R_6$=$R_3$=isopropyl), ritodrine ($R_4$=OH, $R_5$=4-hydroxyphenyl, $R_2$=methyl, $R_6$=$R_3$=2-(4-hydroxyphenyl)ethyl), methamphetamine ($R_4$=H, $R_5$=phenyl, $R_2$=methyl, $R_6$=$R_3$=methyl), fenfluramine ($R_4$=H, $R_5$=3-trifluoromethylphenyl, $R_2$=methyl, $R_6$=$R_3$=ethyl) and propylhexedrine ($R_4$=H, $R_5$=cyclohexyl, $R_2$=methyl, $R_6$=$R_3$=methyl). These compounds are preferably formed using hydrogen and a catalyst as the reductant, although they can be formed using a hydride reducing agent.

According to an alternative embodiment of the invention, the amine (VI) is selected from the group consisting of amphetamine, methoxamine, phenylpropanolamine, hydroxyamphetamine, ethylnorepinepherine and metaraminol. These compounds may be formed using a hydride reducing agent as the reductant.

The reductive amination reaction involves the formation of an imine intermediate prior to the reduction taking place. Accordingly, a second aspect of the present invention provides a method for the formation of an imine of formula (III)

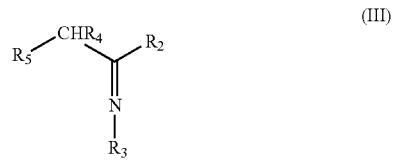

the method comprising reacting a ketone of formula (V) as defined above with an amine of the formula $R_3NH_2$ in which $R_3$ is as defined above, in the presence of a supercritical fluid or a liquefied gas.

In a preferred embodiment of the invention for the synthesis of an amine of formula (VI) in which $R_4$ is OH, hereafter referred to as compound (VIa):

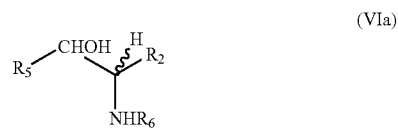

the method involves the preliminary step of forming a ketone of formula (V) in which $R_4$ is OH (hereafter referred to as compound (Va)):

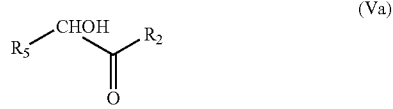

by subjecting an aldehyde of formula $R_5$—CHO to acyloin condensation mediated by yeast with a compound of formula (VIII):

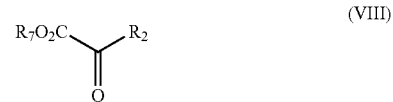

in which $R_2$ is as defined above and $R_7$ is H or alkyl; to yield the ketone of formula (Va), wherein the acyloin condensation step is conducted in the presence of a supercritical fluid or a liquefied gas.

These steps are summarised in the following reaction scheme:

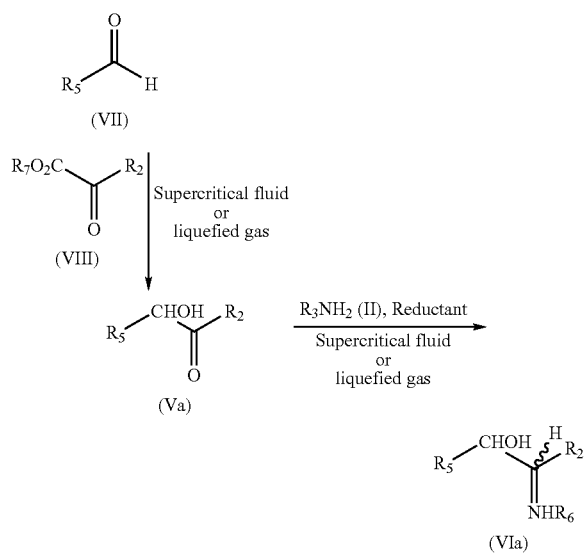

in which:

$R_2$, $R_3$, $R_5$, $R_6$ and $R_7$ are as defined above.

Preferably, the reaction is conducted without isolation or purification of the compound of formula (Va). More preferably, the reactions to form the compound of formula (VIa) from the aldehyde $R_5$—CHO are conducted in one vessel.

Reduction can be effected by any suitable reducing agent. Accordingly, for example, the imine intermediate could be reduced by $LiAlH_4$ (in an appropriate supercritical fluid or liquefied gas medium, which would not be based on $CO_2$ due to possible reaction of $CO_2$ with this reagent) to form a primary amine product. In one embodiment of the invention hydrogen and an appropriate hydrogenation catalyst is used to conduct the reduction. This yields compounds of Formula (VI) in which $R_6$ is the group $R_3$ which comes from the amine reagent $R_3NH_2$. Suitable hydrogenation catalysts include platinum and palladium. Full details concerning appropriate reduction reactions and hydrogenation catalysts for reducing the carbon-nitrogen double bond can be found in S. Patai, *The Chemistry of the Carbon-Nitrogen double bond*, Wiley, New York, 1970, pp276–293 and P. N. Rylander, *Catalytic Hydrogenation over Platinum Metals*, Academic Press, New York, 1967, pp123–138.

In the situation where the reductive amination involves hydrogenation of the imine in the presence of a catalyst, it is preferred that the yeast is recovered from the reaction vessel after the acyloin condensation step, and before the reductive amination, and the catalyst is recovered after the reductive amination.

The amine reagent used in the reductive amination or in the imine formation reaction can be added in any convenient form appropriate for the reaction medium. It may be in the form of a neat solid, liquid or gas, or as a solution in an appropriate solvent. In a preferred embodiment of the invention, it has been found that excellent conversion is obtained when the amine is added in an organic solvent, and the reaction is conducted in a liquefied gas. The organic solvent may in this instance be the same as the liquefied gas.

In all of the broad processes described above, the supercritical fluid may be any supercritical fluid that does not interfere with the reaction. The temperature of the reaction will depend on the properties of the supercritical fluid used and the reagents used in the full reaction sequence. Accordingly, the reaction temperature might be any temperature up to 200° C., preferably up to 50° C., as is appropriate to the reaction. Similarly, the pressure will depend on the properties of the supercritical fluid, and might range from 500 psi (for low critical pressure—supercritical fluids such as sulphur hexafluoride) up to 7000 psi. The critical temperature and pressure of $CO_2$ are 31.1° C. and 1070 psi, respectively. For a procedure that involves a yeast-mediated reaction in the reaction scheme, we have found that carbon dioxide is particularly suitable, as the reaction can be performed at a moderately elevated temperature, suitably between 33 to 42° C., preferably 35° C. At these temperatures, the corresponding pressure may range between 1070 to 2500 psi or higher, preferably 1500 psi.

Other suitable supercritical fluids are as follows:

| Fluid | Critical temperature (° C.) | Critical pressure (psi) |
|---|---|---|
| Ethane | 32.4 | 707.8 |
| Nitrous oxide | 36.6 | 1050 |
| Xenon | 16.7 | 847 |
| Fluoroform ($CHF_3$) | 26.3 | 705 |
| Monofluoromethane | 42 | 812.2 |
| Sulphur hexafluoride | 45.7 | 545.3 |
| Chlorotrifluoromethane | 29 | 561.3 |

It is to be noted that supercritical ammonia is not an appropriate supercritical fluid in which to conduct the reactions, since ammonia may interfere with the reactions. In particular, ammonia may interfere with the imine formation or reductive amination.

When one of the processes described above is performed in the presence of a supercritical fluid, the target compound can be recovered by subjecting the reaction mixture to extraction with a supercritical fluid or an organic solvent such as ethylacetate or diethylether.

Further information regarding equipment design and control and the selection of suitable pressures and temperatures for certain supercritical fluids can be found in *Chemical Synthesis Using Supercritical Fluids* Edited by Philip G Jessop and Walter Leitner.

The liquefied gas may be carbon dioxide, a hydrocarbon such as methane, ethane, propane, butane, ethylene, or the like, or mixtures thereof. Liquefied petroleum gas may be used. Again, the reaction temperature and pressure would be selected taking into account the properties of the liquefied gas being used, and the properties of reaction reagents.

Once the reaction has been completed in liquefied gas, the system is de-gassed and the target compound can be extracted with a supercritical fluid, a liquefied gas or an organic solvent.

As regards the preferred process which involves the preliminary step of a yeast mediated acyloin condensation reaction, it is noted that any yeast capable of effecting the acyloin condensation reaction may be used. It is economically advantageous to use the cheapest yeast available, and ordinary baker's yeast, *Saccharomyces cerevisiae*, is preferred. Strains of yeast adapted to other purposes, including brewing yeast and wine or sherry yeasts could also be employed. Strains specifically adapted to a supercritical fluid environment or for enhanced acyloin condensation efficiency may be used; such strains include conventionallyselected and genetically modified strains. For maximum efficiency of reaction, it is advisable to present the maximum surface area of yeast for contact with the reactants. This can be effected by using "active" dried yeast, which is readily commercially available as "instant dry yeast", and may be stored at room temperature. Alternatively, well-pulverised dry baker's yeast may be used. Other yeasts, such as those described in U.S. Pat. No. 4,734,367, or fungi such as those disclosed in Chênevert et al (1992) may also be used. The person skilled in the art will readily be able to test whether any specific organism will function for the purposes of the invention, using the methods described herein.

While the ratio of yeast to substrate will vary depending on the individual system, and is readily determined experimentally using routine trial and error methods, we have found that for the conversion of benzaldehyde to phenylacetylcarbinol the optimum ratio is 4.2 g yeast/mmol-benzaldehyde; increasing the amount of yeast results in only a small increase in conversion, and lower amounts of yeast provide lower conversion.

Similarly, the optimum reaction time may readily be determined, and for the benzaldehyde-phenylacetyl-carbinol system we have investigated reaction times from 3 to 24 hours. Reactions longer than 24 hours do not lead to higher yields.

The supercritical fluid or liquefied gas used in the process can be recycled. The yeast can be used for other purposes, for example in animal feed, especially when this fluid or gas is carbon dioxide.

As used in the present application, the term "imine" refers to any compound containing a carbon to nitrogen double bond, and therefore this term includes oximes, semicarbazones, and substituted or unsubstituted arylhydrazones (such as 2,4-dinitrophenylhydrazone).

The term "amine" is used herein in its broadest sense to refer to any compound containing a nitrogen atom. The term amine therefore encompasses ammonia, primary, secondary and tertiary amines including alkyl amines, hydroxyamines, alkoxy and aryloxy amines, alkenyl amines, alkynyl amines, amines with silicon-containging substituents such as trimethyl silane, nitrogen-containing heterocyclic compounds, heterocyclyl amines, alkylsulphonyl amines, arylsulphonyl amines, acyl amines (ie amides), alkylthio amines, benzylthio amines, acylthio amines, amines with phosporous-containing substituents, semicarbazides, hydrazines and arylhydrazines, all of which may optionally be substituted with one or more non-deleterious substituent.

Where it is stated that a group may be "substituted", it is to be understood that the group may include one or more substituent selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, and phosphorus-containing groups. Where appropriate, these groups may be protected by suitable protecting groups.

Preferably, the or each substituent is selected from the group consisting of alkyl, aryl, halo; haloalkyl (including trihalomethyl, for one example), nitro, hydroxy, alkoxy, amino, carbonyl, thioxy and thioalkoxy.

The term "alkyl" used either alone or in a compound word such as "optionally substituted alkyl" or denotes straight chain, branched or mono- or poly-cyclic alkyl, preferably $C_{1-18}$ alkyl or cycloalkyl. Examples of straight chain and branched alkyl include methyl, ethyl, propyl, isopropyl, butyl, isbutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimetylpentyl, 1,2-dimethylpentyl, 1,3-dimethylpentyl, 1,4-dimethylpentyl, 1,2,3-trimethylbutyl, 1,1,2-trimethylbutyl, nonyl, 1-, 2-, 3-, 4-, 5-, 6- or 7-methyloctyl, 1-, 2-, 3-, 4- or 5-ethylheptyl, 1-2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like. In some instances the alkyl group is indicated to be of a particular size or length by use of the expression "C1-Cx alkyl". The number of carbon atoms denoted is to be taken to refer to the number of carbon atoms in the alkyl group to the exclusion of any further substituents.

In a preferred embodiment the compound of formula (VIII) (an α-keto carboxylic acid or carboxylic acid ester) is pyruvic acid or a pyruvate buffer (ie $R_2$ is $CH_3$).

In a preferred embodiment of the invention, the compound of formula (VII) is substituted or unsubstituted benzaldehyde, the compound of formula (V) is substituted, or unsubstituted phenylacetylcarbinol, and the compound of formula (VI) is ephedrine or a derivative thereof.

In a particularly preferred embodiment of the invention, there is provided a process for forming ephedrine or a derivative thereof from a substituted or unsubstituted benzaldehyde, the process being in accordance with reaction scheme E:

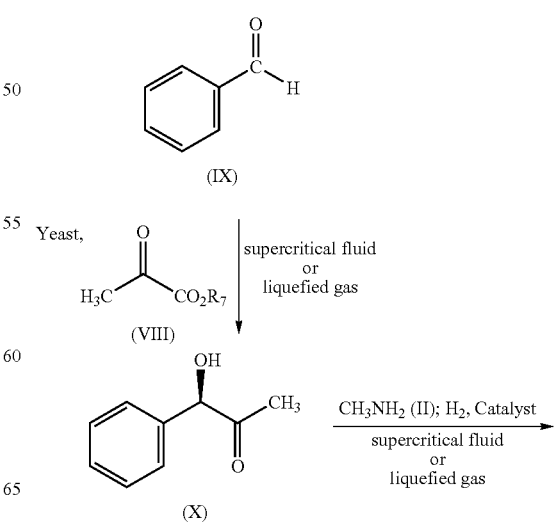

-continued

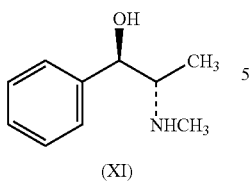

(XI)

wherein $R_7$ is as defined above.

It will be clearly understood that the benzaldehyde (IX), the pyruvic acid (VIII), or both may optionally be substituted, and that pyruvate, for example sodium pyruvate, may be used as an alternative to pyruvic acid. As a further alternative, a precursor of pyruvic acid which can be converted in situ to pyruvic acid may be used, for example, lactic acid, unless the supercritical fluid or liquefied gas is carbon dioxide. Aromatic aldehydes substituted with alkyl, aryl, halo, nitro, hydroxy, alkoxy, amino, carbonyl, thioxy or thioalkoxy groups or composites of these groups may also be used instead of benzaldehyde in this preferred embodiment of the invention.

For either sodium pyruvate or pyruvic acid, the pH of the pyruvate/citrate buffer solution is preferably between 5 and 6, more preferably pH 6. Between 0.6 and 1.2 ml buffer/g of yeast should preferably be used for optimal results.

For the avoidance of any doubt, it is to be understood that when the compound being subjected to reduction includes other functional groups that can be reduced by the subject reducing agent, the corresponding target compound (defined or described by words or chemical structure) should be interpreted to include corresponding compounds including reduced functional groups in place of the original functional groups.

According to the present invention there is also provided a compound prepared by any one of the processes described above.

EXAMPLES

The invention will now be described in further detail by way of reference only to the following non-limiting examples.

Example 1

Reaction in Supercritical Carbon Dioxide Using Liquid Methylamine

Phenylacetylcarbinol (0.2 g, 1.3 mmol), palladium catalyst (0.05 g) and liquid methylamine (3 mls) were placed into a 250 ml stainless steel pressure vessel. The vessel was pressurised up to 400 psi with hydrogen gas and then up to a total of 1500 psi by pumping dried liquid carbon dioxide into the vessel. The vessel was then stirred in a 35° C. water bath for 24 h. After 24 h, the reaction vessel was cooled to room temperature and slowly de-gassed. The vessel contents and residue was washed three times with diethyl ether and filtered. Gas chromatography analysis revealed 78% conversion of phenylacetylcarbinol (PAC) to ephedrine.

Example 2

Reaction in Supercritical Carbon Dioxide Using Methylamine in THF

Phenylacetylcarbinol (0.2 g, 1.3 mmol), palladium catalyst (0.05 g) and 5 fold excess of 2.0M methylamine in THF (3.125 mls, 6.45 mmol) were placed into a 250 ml stainless steel pressure vessel. The vessel was pressurised up to 400 psi with hydrogen gas and then up to a total of 1500 psi by pumping dried liquid carbon dioxide into the vessel. The vessel was then stirred in a 35° C. water bath for 24 h. After 24 h, the reaction vessel was cooled to room temperature and slowly de-gassed. The vessel contents and residue was washed three times with diethyl ether and filtered. Gas chromatography analysis revealed 46% conversion of phenylacetylcarbinol (PAC) to ephedrine.

Example 3

Reaction in Supercritical Carbon Dioxide Using Gaseous Methylamine

Phenylacetylcarbinol (0.2 g, 1.3 mmol), palladium catalyst (0.05 g) were placed into a 250 ml stainless steel pressure vessel. Anhydrous gaseous methylamine was vented into the vessel to a pressure of approximately 100 psi. The vessel was then pressurised up to 400 psi with hydrogen gas and up to a final pressure of 1500 psi by pumping dried liquid carbon dioxide into the vessel. The vessel was then stirred in a 35° C. water bath for 24 h. After 24 h, the reaction vessel was cooled to room temperature and slowly de-gassed. The vessel contents and residue was washed three times with diethyl ether and filtered. Gas chromatography analysis revealed 32% conversion of phenylacetylcarbinol (PAC) to ephedrine.

Example 4

Reaction in Liquid Carbon Dioxide Using Liquid Methylamine

Phenylacetylcarbinol (0.2 g, 1.3 mmol), palladium catalyst (0.05 g), liquid methylamine (3 mls) were placed into a 250 ml stainless steel pressure vessel. The vessel was pressurised up to 400 psi with hydrogen gas and then up to a total of 1500 psi by pumping dried liquid carbon dioxide into the vessel. The vessel was then stirred at room temperature for 24 h. After 24 h, the reaction vessel was slowly de-gassed. The vessel contents and residue was washed three times with diethyl ether and filtered. Gas chromatography analysis revealed 63% conversion of phenylacetylcarbinol (PAC) to ephedrine.

Example 5

Reaction in Liquid Carbon Dioxide Using Methylamine in THF

Phenylacetylcarbinol (0.2 g, 1.3 mmol), palladium catalyst (0.05 g) and 5 fold excess of 2.0M methylamine in THF (3.125 mls, 6.45 mmol) were placed into a 250 ml stainless steel pressure vessel. The vessel was pressurised up to 400 psi with hydrogen gas and then up to a total of 1500 psi by pumping dried liquid carbon dioxide into the vessel. The vessel was then stirred at room temperature for 24 h. After 24 h, the reaction vessel was slowly de-gassed. The vessel contents and residue was washed three times with diethyl ether and filtered. Gas chromatography analysis revealed 97% conversion of phenylacetylcarbinol (PAC) to ephedrine.

Example 6

Combined Yeast-Mediated Acyloin Condensation of Benzaldehyde and Reductive Amination to Form Ephedrine Benzaldehyde (0.137 g, 1.3 mmol), sodium pyruvate (2.168 g, 19.7 mmol), pH 6 citrate buffer (5.4 ml) and yeast (5.4 g) were placed into a 250 ml stainless steel pressure vessel. This vessel was pressurised to 1500 psi by pumping dried liquid carbon dioxide into the vessel. The vessel was then stirred in a 35° C. water bath for 24 h. After 24 h, the reaction vessel was cooled to room temperature and slowly de-gassed.

Phenylacetylcarbinol (0.2 g, 1.3 mmol), palladium catalyst (0.05 g) and 5 fold excess of 2.0M methylamine in THF (3.125 mls, 6.45 mmol) was then placed into the stainless steel pressure vessel. The vessel was pressurised up to 400 psi with hydrogen gas and then up to a total of 1500 psi by pumping dried liquid carbon dioxide into the vessel. The vessel was then stirred in a 35° C. water bath for 24 h. After 24 h, the reaction vessel was cooled to room temperature and slowly de-gassed. The vessel contents and residue was washed three times with diethyl ether and filtered. Gas chromatography analysis revealed 60% conversion of phenylacetylcarbinol (PAC) to ephedrine.

It will be understood by persons skilled in the art that various modifications may be made to the embodiments and examples described above without departing from the scope of the invention.

The claims defining the invention are as follows:

1. A method for the preparation of a compound of formula (VIa):

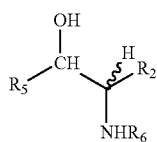
(VIa)

in which
R$_2$ is an optionally substituted C1–C6 alkyl;
R$_5$ is an optionally substituted aryl, an optionally substituted aralkyl, or an optionally substituted alkyl; and
R$_6$ is H or an optionally substituted C1–C6 alkyl;
the method including:
(i) subjecting an aldehyde of formula R$_5$—CHO to acyloin condensation mediated by yeast with a compound of formula (VIII):

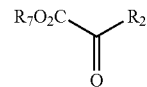
(VIII)

in which R$_2$ is as defined above and R$_7$ is H or alkyl; to yield the ketone of formula (Va):

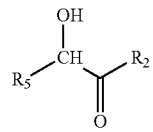
(Va)

in which R$_5$ and R$_2$ are as defined above; and
(ii) subjecting the ketone of formula Va to reductive amination with an amine of formula R$_3$NH$_2$ in which R$_3$ is an optionally substituted alkyl, and a reductant, to form the compound of formula (VIa),
wherein reactions (i) and (ii) are conducted in the presence of a supercritical fluid or a liquefied gas.

2. The method according to claim 1, wherein the reductant is hydrogen and the reduction is conducted in the presence of a catalyst.

3. The method according to claim 2, wherein the catalyst is platinum or palladium.

4. The method according to claim 1, wherein the reductant is a hydride reducing agent.

5. The method according to claim 1, wherein the compound of formula (VIa) is selected from the group consisting of ephedrine (R$_4$=OH, R$_5$=phenyl, R$_2$=methyl, R$_6$=R$_3$=methyl), isoetharine (R$_4$=OH, R$_5$=3,4-dihydroxyphenyl, R$_2$=ethyl, R$_6$=R$_3$=isopropyl), and ritodrine (R$_4$=OH, R$_5$=4-hydroxyphenyl, R$_2$=methyl, R$_6$=R$_3$=2-(4-hydroxyphenyl)ethyl).

6. The method according to claim 1, wherein the amine (VIa) is selected from the group consisting of methoxamine (R$_4$=OH, R$_5$=dimethoxyphenyl, R$_2$=methyl, R$_6$=H), phenylpropanolamine (R$_4$=OH, R$_5$=phenyl, R$_2$=methyl, R$_6$=H), ethylnorepinepherine (R$_4$=OH, R$_5$=3,4-dihydroxyphenyl, R$_2$=methyl, R$_6$=H) and metaraminol (R$_4$=OH, R$_5$=3-hydroxyphenyl, R$_2$=methyl, R$_6$=H).

7. The method according to claim 1, wherein the reaction temperature of reaction (ii) is 200° C. or less.

8. The method according to claim 7, wherein the reaction temperature of reaction (ii) is 50° C. or less.

9. The method according to claim 1, wherein reaction (ii) is conducted at a pressure of between 500 psi and 7000 psi.

10. The method according to claim 1, wherein the supercritical fluid is selected from the group consisting of carbon dioxide, ethane, nitrous oxide, xenon, fluoroform (CHF3), monofluoromethane, sulphur hexafluoride and chlorotrifluoromethane.

11. The method as claimed in claim 10, comprising recovering the compound of formula (VIa) by subjecting the reaction mixture to extraction with a supercritical fluid or an organic solvent.

12. The method as claimed in claim 1, wherein the reductive amination is conducted in a liquefied gas selected from the group consisting of liquefied carbon dioxide or a liquefied hydrocarbon gas.

13. The method as claimed in claim 12, comprising de-gassing the vessel in which the reductive amination was conducted after completion of the reaction, and extracting the compound of formula (VIa) with a supercritical fluid, a liquefied gas or an organic solvent.

14. The method as claimed in claim 12, wherein the reductive amination is conducted in liquid carbon dioxide at a pressure of between 1070 to 2500 psi.

15. The method according to claim 12, wherein the amine $R_3NH_2$ is added to the reaction in an organic solvent.

16. The method as claimed in claim 1, comprising recycling the supercritical fluid or liquefied gas.

17. The method as claimed in claim 1, wherein the yeast is *Saccharomyces cerevisiae*.

18. The method as claimed in claim 1, wherein $R_5$—CHO is benzaldehyde ($R_5$ is phenyl) and $R_2$ is methyl, and the yeast is added in an amount of about 4.2 g yeast/mmol benzaldehyde.

19. The method as claimed in claim 18, wherein the acyloin condensation reaction is conducted over a period of between 3 and 24 hours.

* * * * *